(12) United States Patent
Chavez et al.

(10) Patent No.: US 6,713,764 B2
(45) Date of Patent: Mar. 30, 2004

(54) FIELD BASED SPECTRAL RADIOMETER

(75) Inventors: Pat Chavez, Flagstaff, AZ (US); Stuart C. Sides, Flagstaff, AZ (US)

(73) Assignee: The United States of America as represented by The Department of Interior, Washington, DC (US)

( * ) Notice: Subject to any disclaimer, the term of this patent is extended or adjusted under 35 U.S.C. 154(b) by 133 days.

(21) Appl. No.: 10/073,323

(22) Filed: Feb. 13, 2002

(65) Prior Publication Data

US 2003/0150992 A1 Aug. 14, 2003

(51) Int. Cl.$^7$ .................................................. G01J 3/00
(52) U.S. Cl. ............................. 250/339.05; 250/339.01
(58) Field of Search ....................... 250/339.01, 339.05, 250/338.1, 336.1

(56) References Cited

U.S. PATENT DOCUMENTS 6,161,075 A * 12/2000 Cohen .......................... 702/3

* cited by examiner

Primary Examiner—David Porta
Assistant Examiner—Christine Sung
(74) Attorney, Agent, or Firm—Mark Homer

(57) ABSTRACT

A robust two spectral band radiometer for long-term stand-alone spectral radiance measurements in the field is provided. The instrument can be used to monitor various surface parameters over prolonged periods of time by automatically collecting spectral radiance measurements at a user selected time interval (minutes to days). Two main applications are the monitoring of water surface parameters, such as total SSC and turbidity, and on-land vegetation by collecting spectral radiance measurements in a broad visible red and near-infrared spectral bands. Use for other application is possible using different spectral bands and multiple radiometers. Also included is the use of a ratioing technique to correlate the spectral radiance values rather than spectral reflectance values to the surface parameters of interest; this simplifies both the filed instrumentation requirements and post processing procedures.

12 Claims, 1 Drawing Sheet

FIELD BASED SPECTRAL RADIOMETER

FIELD OF THE INVENTION

This invention relates to a spectral radiometer designed to be left in the field on a stand-alone basis for prolonged periods of time (months to years) to measure the spectral characteristics of various earth surface targets in two bands.

BACKGROUND OF THE INVENTION

For several decades, spectral radiance data have been used to help map and monitor the earth's surface. The advent of civilian satellite imaging systems in the early 1970s propelled this technology into widespread use both in image format and in situ field measurements. Digital imaging systems carried on-board earth-orbiting satellites collect images using optical systems that record the earth surface spectral characteristics in various bands (e.g., the brightness/color in visible and near-infrared (NIR) spectral bands). Current satellite imaging systems have expanded spectral band coverage compared to those used in the 1970s and early 80s (e.g., short-wave IR—SWIR), resulting in the need for more sophisticated field instruments with increased spectral measurement capabilities. In order to help identify the design of future satellite imaging sensors and to collect spectral radiance data in the field for use with current state-of-the-art satellite and airborne imaging systems, the need to design and build more complex and sophisticated spectral radiometers for in-the-field use has driven both the cost and constraints of such an instrument quite high. The cost of spectral radiometers now range from $12K to $80K for field instruments that can collect data up to 1024 spectral bands. For applications that require only a few bands (e.g., 2 to 6), with a high temporal resolution over a prolonged period of time, using a current state-of-the-art spectral radiometer is out of the question. Both in cost and design the currently available spectral radiometers are not made for long-term stand-alone field use. Therefore, they are used only for short-term studies and applications while the user is in the field, meaning that they cannot provide the high temporal resolution needed for long-term studies and operational monitoring of the earth's surface.

Spectral radiometers were developed for in-the-field use for remote sensing in the early 1970s. Radiometers with four broad spectral bands were designed first, then the number of spectral bands began to increase and the band width to decrease to allow better total spectral measurements to be collected of the cover types of interest (i.e., soils, vegetation, or water). In the late 1980s and early 1990s, spectral radiometers having over 250 narrow spectral bands were designed and built and now ones with 512 to 1024 bands (hyper-spectral) are becoming the standard. However, there are a number of problems with the use of current hyper-spectral radiometers, including:

1) The amount of data they are designed to collect is typically an "overkill" for many applications and operational monitoring of the earth's surface (e.g., surface waters and general vegetation cover). That is, over 500 bands of spectral radiance data are not needed for many applications, especially for non-research operational and monitoring uses.

2) The cost for the much more complex and sophisticated instruments now on the market ranges from $12,000 to $80,000. This cost is quite high for most non-research applications, especially if several to tens of them are needed for good spatial monitoring over a regional area.

3) The spectral radiometers currently on the market are designed to be used in the field for a relatively short amount of time by a person while doing fieldwork. Current radiometers are not designed to be left in the field for long periods of time (i.e, months to years) in a stand-alone node to automatically collect spectral radiance data with a high temporal resolution.

4) The current spectral radiometers with over 500 bands have narrow bandwidth, so the overall signal-to-noise ratio is low compared to the more broadband width radiometers. Therefore, for low radiance targets, such as surface waters, the noise levels will typically be higher than for those collected by a less complex broadband radiometer.

5) A spectral radiometer with four bands was developed in the early 1970s by Exotech, Inc., for use in the field while the operator was present; it is not designed to be left in the field on a stand-alone basis for prolong periods of time.

Satellite image data can be used to monitor various features on the earth's surface with additional spectral windows. However, major problems with using satellite image data to monitor surface water parameters, and on-land vegetation cover, are that the combination of temporal and spatial resolutions often needed are well beyond the capability of current satellite imaging systems. To obtain the temporal resolution needed of minutes to hours, and a spatial resolution of one to three meters required to see the surface waters of rivers, or for daily monitoring of vegetation within a small area, a field based instrument is required.

A number of other types of radiometers have been disclosed which have been used for a variety of purposes.

Goetz et al., in U.S. Pat. No. 4,345,840, disclose a hand held, self-contained dual beam rationing radiometer for identifying selected materials that reflect radiation within a predetermined band, preferably in the IR or visible range. The apparatus includes two pivoting optical trains directed toward the same target. Each train has a separate filter for selection of the narrow spectral bands to be ratioed, by means of a dividing circuit, to identify a particular substance based on its known spectral characteristics.

Spiering et al., in U.S. Pat. No. 6,020,587, disclose a device for measuring plant chlorophyll content by collecting light reflected from a target plant. A beam splitter separates the light into distinct wavelength bands or channels. Photodetectors and amplifiers within the device then process the bands, converting them into electrical signals.

Gupta discloses, in U.S. Pat. No. 4,996,430, a device for distinguishing target objects having substantially identical reflectance ratios for two separated wavelengths (lambda-1, lambda-2), from background objects possessing different reflectance values for the same two wavelengths. This device includes an active optical sensor with first and second transmitters that transmit signals at wavelengths of lambda-1 and lambda-2, respectively. When the transmitted signals reflect off of an object, a receiver senses the reflected signals, which are then processed through a high-speed preamplifier and amplifier, producing voltages V1 and V2 at the receiver's output. A conventional ratio calculating circuit then calculates a ratio of V1 and V2, which is then compared to a predetermined threshold value.

Levin et al., in U.S. Pat. No. 6,031,233, disclose a handheld spectrometer for identifying samples based upon their IR reflectance. The device includes a window and adjacent optical bench. The optics, which align directly with the sample under investigation, consist of a broad band IR light shining onto an acousto-optic tunable filter crystal, the latter passing narrow band IR light with a swept frequency; a lens focusing the IR light through the window onto the sample; and a reflectance detector aligned with the housing window to detect light reflected from the sample. A computer mounted in the housing compares the reflectance spectrum with stored data and identifies the sample material.

Novison, in U.S. Pat. No. 5,527,062, discloses a portable IR spectrophotometer for testing samples of organic construction materials. A single source of IR light is divided into two beams. The first beam is directed to the surface of the target sample, from which the light is reflected at least four times. The second reference beam is directed toward a neutral surface. The two beams are then combined and focused onto a detector element. The detector output is proportional to the energy absorbed by the test sample. A pen recorder attached to the apparatus generates a graphic "fingerprint" of the sample's reflectance spectrum.

Typically, spectral bands used to study and monitor water parameters fall within the blue and green spectral bands, not red and near IR as to be used in this application.

Traditionally, spectral radiance measurements must be converted to surface reflectance, requiring a more complicated setup and additional instrument capabilities in the form of a calibrator or a solar irradiance measurement. By ratioing the spectral radiances of two bands, as to be done in this design, the need to collect measurements of either a calibrator or solar irradiance at the same time the target surface readings are collected is not needed.

SUMMARY OF THE INVENTION

A main objective of the present invention is to overcome the deficiencies in the existing instruments and to provide a robust, dual-band spectral radiometer suited for long-term stand-alone field use. By using the ratio of spectral radiance values to correlate to the parameters of interest, rather than spectral reflectance values as is typically used, it eliminates the need for either calibrator or solar irradiance measurements, thereby reducing the cost and complication encountered when these extra measurements are needed. Two immediate applications of this design will be to measure and monitor the spectral characteristics of water surfaces, which can be correlated to water parameters such as total suspended sediment concentration (total SSC) and turbidity, and on-land vegetation spectral signatures, which can be correlated to vegetation cover/density, with possible correlation to vegetation health/water stress.

This invention includes a method to effect water surface and on-land vegetation long-term stand-alone monitoring by utilizing the same two spectral bands. For these applications the two spectral bands have a broadband width and cover the visible red and near-IR portions of the spectrum. However, the spectral radiometer's general design is such that for other applications that will arise a different set/pair of two bands can be used (e.g., blue and red, and/or narrow instead of broad band widths). Also, if it is determined that some applications required more than two bands (e.g., five or six), then sets of this radiometer can be used (2 bands per radiometer times 3 radiometers will allow a six band set up, if needed).

Again, another main objective of the invention or method is to provide a means to correlate spectral data collected in the field with this instrument to surface parameters of interest, such as total SSC or vegetation density, without the need to also collect spectral measurements of a calibrator or solar irradiance at the same time.

This invention includes a new procedure that uses the ratio of measured spectral radiances in two bands. In the case of surface waters and on-land vegetation it uses broad bands in the visible red and near-IR portions of the spectrum, for long-term operational monitoring of the parameters of interest. The ratio of the spectral radiances in two bands has a direct and high correlation to the ratio of reflectance values, therefore, this can often serve as a replacement to using actual surface reflectance in the correlation of the spectral measurements to the surface parameter of interest. This means the need for either a calibrator or solar irradiance measurements to be collected at the same time is eliminated, thus making the procedure both less expensive and less complex than procedures that use reflectance values. It should be noted that if either a calibrator or solar irradiance measurements are needed, the maintenance requirements of a long-term stand-alone set up will dramatically increase. This will be because the calibrator or the sky looking optics will need to be kept clean so the measurements are reliable and comparable from day-to-day.

The instrument in the present invention is designed to collect spectral radiance measurements in two bands. For the surface waters and on-land vegetation monitoring applications it will use broad-width bands in the visible red and near-infrared portions of the spectrum. The spectral radiance values from these two broad-width bands have a good correlation with several surface water parameters, including total suspended sediment concentration (total SSC) related to silt and clay as well as turbidity, on both inland and coastal waters. The spectral radiance values from these same two spectral bands also have a good correlation with vegetation cover or density, and have been shown to often correlate with vegetation maturity and, in some cases, vegetation health—water stress.

Two immediate applications of the instrument are to measure the spectral characteristics of water surfaces or on-land vegetation to map and monitor the total suspended sediment concentrations and turbidity of water or vegetation cover/density.

DETAILED DESCRIPTION OF THE INVENTION

Figure 1:
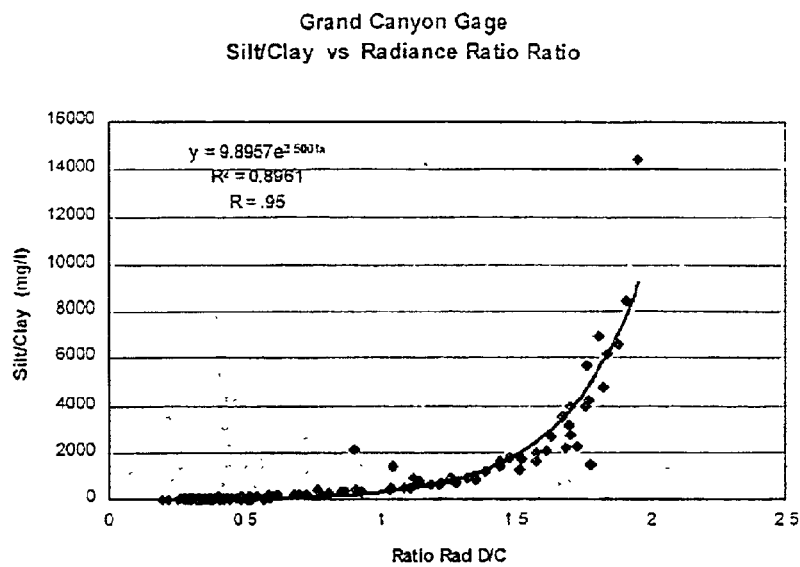
FIG. 1 shows the correlation between silt/clay and irradiance.

The instrument of this invention is a simple but robust two spectral band radiometer that can be used in the field on a long-term (months to years) stand-alone basis to automatically collect high temporal resolution data directly related to the spectral radiance characteristics of the target/surface it is set up to monitor. The data will be useful for both operational monitoring to detect change, as well as for research studies that require this type of information. Two immediate applications for this instrument and the spectral radiance post-processing procedure included in the invention are the monitoring of surface in-land waters for total suspended sediment concentrations and turbidity, as well as the on-land vegetation cover. The sampling temporal resolution can be selected by the user and will typically be depended on the application (e.g., every 15 to 30 minutes for surface water monitoring and once per day or week for on-land vegetation monitoring). For applications needing more than two spectral bands, but still on the order of fewer than ten, multiple instruments can be set up with a different pair of spectral bands for each radiometer.

The instrument of this invention can be installed either as a single unit or in groups in the field for prolonged periods of times (i.e., months to years), to collect spectral radiance measurements on a relatively high temporal frequency/resolution. The temporal resolution needed will depend on the application and can be selected by the individual user. The temporal resolution can range from a measurement collected every few minutes to every few days (e.g., every 15 minutes for surface water monitoring to once per day or per week for monitoring on-land vegetation). The direct output of the instrument is voltages for the two bands that are post-processed to convert to spectral radiance values. The spectral radiance values are then ratioed to effect a first order removal of the effect of both sun elevation and cloud cover variations encountered throughout the day and year. After the initial correlation of the resulting ratio values to the parameter of interest, for example water sample analyses results or field vegetation transect information, new values can be used to monitor the surface parameters of interest (total SSC and/or turbidity in the case of surface waters or changes in vegetation spectral signature in on-land setting).

The two bands that will be used for both the surface water and on-land vegetation monitoring, that is broad-width bands in the visible red and near-infrared portions of the spectrum, are widely used by the remote sensing community to study and map vegetation, but their application to surface water monitoring is typically not used and is a new application of this invention (typically the blue and green portions of the spectrum are used). Another major difference in the procedure of the present invention is the use of spectral radiance rather than spectral reflectance values for analysis and monitoring. Since spectral radiance measurements in the field are collected under various sun elevations and shading conditions, existing procedures convert the data to spectral reflectance values to normalize for the variable lighting conditions before using them in analysis and monitoring applications (i.e., spectral reflectance values are, to a first order, independent of lighting conditions). However, a disadvantage of using spectral reflectance values is that a second set of spectral radiance measurements must be made at the same time that target measurements are made. Measurements of either a bright standard calibrator or solar irradiance in the bands being used must be made at the same time to allow the radiance values to be converted into spectral reflectance values. This makes the collection of the data in the field more complicated and increases the expense and complexity of the instrument needed. In fact, besides increasing the complexity in collecting the data for long-term stand-alone data collection requirements, this becomes a major problem and could make the collection of data over a long-term basis not reasonable. The reason for this is the requirement to keep the calibrator or the sky ward sensing optics clean so that readings are not affected by dirty surfaces; this can become a major maintenance problem, especially when the radiometer is set-up in remote areas.

The procedure of the present invention circumvents this problem by using the ratio of the spectral radiance values (i.e., correlate the ratio of two bands to the surface parameter of interest, rather than the individual band spectral values). It turns out the ratio of spectral radiance values is highly correlated to the ratio of the spectral reflectance values (this is shown in the equations below), therefore, rather than developing a model that correlates spectral reflectance values to the parameter of interest (as is usually done), one can use the ratio of spectral radiance values. By using the ratio of the spectral radiance values when correlating to the desired surface parameters (e.g., total SSC, turbidity, or vegetation density), there is no need to convert to surface reflectance values, thereby eliminating the need for either a calibrator or sky solar irradiance measurements. The use of ratio spectral radiance values of two bands close to each other, such as in the present invention, automatically eliminates, to a first order, most problems associated with changing sun/shade conditions encountered throughout the day or the year, and the resulting spectral radiance ratio is highly correlated to spectral reflectance ratio values.

Specifically, provided below (see equation 1) is a general equation widely used to convert spectral radiance to spectral reflectance values. Also shown, is the novel equation (equation 3) used in the procedure of the present invention to demonstrate that the correlation between the ratio of spectral reflectance and the ratio of spectral radiance values are highly correlated, therefore, either one can be used when a relationship exists between one of them and a surface parameter of interest (e.g., total SSC, turbidity, or vegetation density). This is important because spectral radiances can be measured using simplified techniques compared to spectral reflectances.

$$\text{Reflectance} = [\Pi * D * D * (Rad - HazeRad)] / (E_o * \cos N) \quad (1)$$

where

Reflectance=Surface reflectance in the given spectral band $\Pi$=3.14259 (pi)

D=Sun-Earth distance in AU (approx. 0.98 to 1.02)

Rad=Radiance in the given spectral band (radiance is equal to at-satellite values if dealing with satellite borne images, however, with ground based readings, such as in our case, it is equal to the actual surface/target radiance)

HazeRad=Atmospheric haze radiance; equal to zero for field or on the ground readings N=Solar zenith angle, measured in degrees (90 minus sun elevation angle)

$E_o$=Total solar irradiance in the given spectral band

To convert spectral radiance data collected in the field/on the ground to spectral reflectance values, spectral radiance measurements must also be collected at the same time in the same bands of either a bright calibrator that has a known reflectance or incoming solar irradiance (Eo in equation 1) in the bands being used. The calibrator or incoming solar irradiance measurements gives the information required to covert to reflectance values, thereby, correcting for differences in lighting conditions (i.e., sunny or shaded conditions, as well as differences in sun elevation angles throughout the day or year), as well as the earth-sun differences (Eo and D terms in equation 1). In order to eliminate the need for the extra measurements, which requires either a second radiometer if a calibrator option is used or a more complex design if only a single radiometer is used, a new procedure has been developed that uses the ratio of the spectral radiances of the two bands instead to develop the model/relationship needed for the parameters of interest. Keep in mind, that for long-term stand-alone stations the calibrator or sky ward pointing optics might not be an option because of the question of keeping the surfaces clean over a period of weeks to months between field visit. Solving equation (1) for in-the-field radiance gives:

$$Rad = (\text{Reflectance} * Eo * \cos N) / (pi * D * D) \quad (2)$$

The HazeRad term in equation 1 is equal to zero on the ground because of the lack of atmospheric haze effects compared to imaging from space, so it is dropped and not present in equation 2. Using equation 2, the radiance of two spectral bands, for example the red and near-IR bands, collected simultaneously by the radiometer can be put into the radiance radio algorithm as follows:

$$\frac{Rad_{red}}{Rad_{near-IR}} = \frac{Reflectance_{red} * E_{ored} * \text{CosN}/(\pi * D * D)}{Reflectance_{near-IR} * E_{onear-IR} * \text{CosN}/(\pi * D * D)} \quad (3)$$

The CosN, Π, and D terms cancel, so the effect of sun elevation (CosN) and earth-sun distance (D) they represent is automatically eliminated. The radiance ratio is thus reduced to equation (4), below:

$$\frac{Rad_{red}}{Rad_{near-IR}} = \frac{Reflectance_{red} * E_{o(red)}}{Reflectance_{near-IR} * E_{o(near-IR)}} \quad (4)$$

The values $E_{o(red)}$ and $E_{o(near-IR)}$ increase and decrease together in accordance with variations in sun elevation and shading conditions, which is influenced by the both the time of day and year. To a first order the value of the ratio of $E_{o(red)}$ to $E_{o(near-IR)}$ is approximately constant. Thus, the ratio of spectral radiance values, which can be generated without the need for a calibrator or solar irradiance measurements, correlate directly with the ratio of spectral reflectance values. Therefore, a major advantage of using the ratio of spectral radiance values to generate the model/ relationship required, rather than spectral reflectance values, is that neither a calibrator or solar irradiance measurements are needed—this reduces the design and complexity requirements of the field instrument and its set up by removing the need to keep the surface of either a calibrator or sky viewing optics clean over a prolonged period of time. Because the spectral radiance ratio is highly correlated to the spectral reflectance ratio of the target of interest (e.g., surface water or on-land vegetation), the spectral radiance ratio shown in equation (4) is used in this procedure in place of reflectance values that require a calibrator or sky viewing optics. Consequently, the present invention eliminates the need for more complicated instrument requirements and set-up traditionally needed to monitor surface parameters of interest. The present invention makes available a procedure that can be used in the field to monitor changes in various surface spectral characteristics for prolonged periods of time without the need for frequent maintenance requirements (to keep the calibrator or skyward pointing optics clean). In two immediate applications dealing with surface waters and on-land vegetation broad bands in the red and near-infrared portions of the spectrum are used. However, in other applications two other bands can be used instead, depending on the application. Also, if more than two bands are needed to appropriately monitor the spectral properties of a surface, a combination of two to several of the new radiometers can be used. For example, if a user wants to monitor the atmosphere for hazy/pollution changes a radiometer with two bands in the lower blue and lower green portions of the spectrum could be used (or blue and red spectral bands), and they can be more narrow than the ones being used for the above two immediate applications. If it is found that 3 to 5 more narrow bands are needed to monitor the parameter of interest, then two or three radiometers, with two narrower bands per radiometer can be used in the field set up.

Again, the use of this new robust spectral radiometer and the ratio of spectral radiances (rather than reflectance as is common) to help map and monitor various earth surface parameters has the following advantages: designed for long-term stand-alone field use, collects spectral measurements having a relatively high temporal frequency/resolution (e.g., every 15 min. to twice per day to once per week), low cost compared to existing instruments, option to use as few as only two spectral bands with the option of setting up more than one instrument for applications needing more than two bands, data can be correlated to satellite images, plus the spectral data can be correlated to the parameters of interest without the need to use a calibrator or measure incoming solar irradiance because it works with the ratio of the spectral radiance values rather than spectral reflectance.

An Exotech four band spectral radiometer was used to collect spectral radiance measurements of the surface waters on the Colorado River at the bottom of the Grand Canyon. This radiometer was designed and developed in the early 1970s and contains broad blue, green, red, and near-infrared bands. The radiometer was protected from rain and direct sunlight in an attempt to design an initial version of a stand-alone long-term instrument. The spectral radiance data collected using this radiometer set up, which was not designed for long-term stand alone use, were correlated to total suspended sediment, silt/clay, and sand concentrations (mg/l) derived from water samples collected during the spectral radiance measurements. The correlation between the spectral measurements and both total SSC and silt/clay of the water samples was very good with an R value of 0.95, while the correlation with sand was not nearly as good with an R value of only about 0.60. FIG. 1 shows the relationship between silt/clay and radiance ratio (basically identical to total SSC); the model derived for this particular data set to relate spectral radiance values to silt/clay concentrations is:

Silt/clay=9.8957*exp(3.5*spectral radiance ratio)

Figure 2:
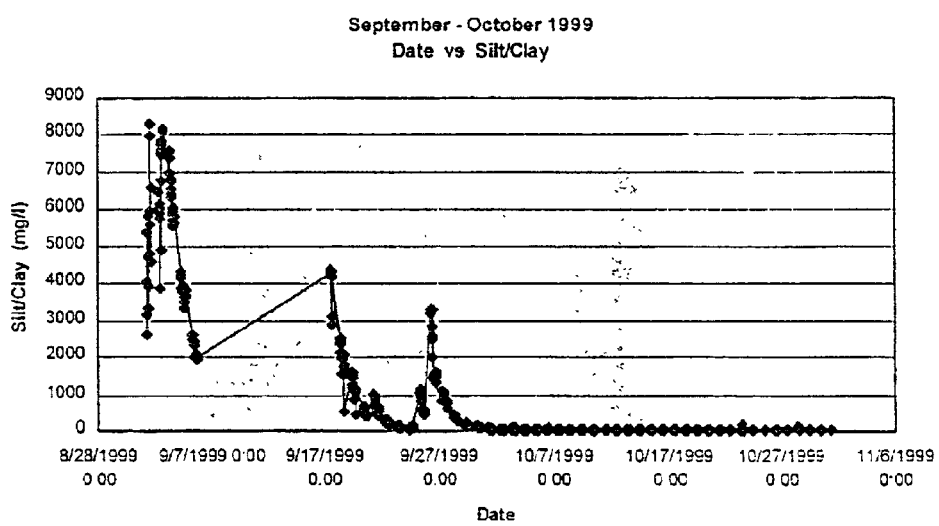
FIG. 2 shows total SSC collected over a two month period.

This model was used to predict the silt/clay (and total SSC) for measurements collected during the time water sample results were not collected. FIG. 2 is a graph showing the total SSC for the time period covering September to October 1999. This has been compared to the same time period in 2000 and a signature difference due to monsoon rain differences between the two years is easily detected.

Operational monitoring of total SSC and silt/clay with this level of temporal resolutions and length of time are not typical, and to do it with an instrument that physically does not touch the water, which dramatically reduces the maintenance requirements, has not previously been done. This is an example of the potential of this instrument for high temporal resolution long-term automatic data collection for both operational monitoring and research applications.

The Exotech radiometer used in this experiment was designed and built in the early 1970s, so in the design of this new simple, but robust, radiometer we take advantage of the new technology that is now available. For example, the design of the new radiometer is such that it can be set up to either pass the voltages measured (which are directly related to spectral radiances) directly to a data logger and have it store the values offline, or make use of the new flash card technology to store the values within the radiometer unit. The values can then be downloaded at a later date onto external storage using a laptop computer. The option selected will depend on the set up; that is, will it be a unit that is the only one being used at that location (this would probably use the internal flash card option), or is this one of several instruments set up at that location (this set up would probably prefer the outside data storage option because a data logger is already available). By having this option the extra cost of a data logger device can be eliminated when the instrument is the only one being used at that location.

In the single instrument mode the instrument will also require the capability to have internally an analog-to-digital conversion capability. The multi-instrument mode this conversion can be done by the external data logger.

The instruments will be equipped with the option of either manual or automatic gain settings. In the manual settings the gain for each of the two spectral bands is pre-selected and used at all times. In the automatic mode if the light levels being measured are too low, the gain is automatically increased to get the reading into a desired range, then the selected gain values are used to collect the measurements at that time; the gain values used are recorded for post processing purposes. The next time it makes a measurement the gains are again automatically optimized for the brightness/radiance levels encountered at that time.

In the two immediate applications that the instrument will be used, that is to help monitor surface waters and on-land vegetation, the two spectral bands to be used correspond to those used to compute the widely popular Normalized Difference Vegetation Index (NVDI) from multi-spectral satellite and airborne image data. Therefore, the instrument with this particular two band combination will give those studying and monitoring vegetation growth and density a tool to collect long-term high temporal resolution in-the-field data automatically without needing to be present during the data collection.

The foregoing description of the specific embodiments will so fully reveal the general nature of the invention that others can, by applying current knowledge, readily modify and/or adapt for various applications such specific embodiments without undue experimentation and without departing from the generic concept. Therefore, such adaptations and modifications should and are intended to be comprehended within the meaning and range of equivalents of the disclosed embodiments. It is to be understood that the phraseology or terminology employed herein is for the purpose of description and not of limitation. The means and materials for carrying our various disclosed functions make take a variety of alternative forms without departing from the invention. Thus, the expressions "means to . . . " and "means for . . . " as may be found in the specification above and/or in the claims below, followed by a functional statement, are intended to define and cover whatever structural, physical, chemical, or electrical element or structures which may now or in the future exist for carrying out the recited function, whether or not precisely equivalent to the embodiment or embodiments disclosed in the specification above; and it is intended that such expressions be given their broadest interpretation.

What is claimed is:

1. A method for monitoring surface parameters comprising collecting spectral radiance measurements in two spectral bands;

applying ratioing techniques to the spectral radiance measurements to remove the effect of sun elevation and cloud cover variations and obtain a ratio of spectral radiance measurements wherein the ratio of spectral radiance measurements comprise a direct correlation to spectral reflectance values;

monitoring the surface parameters of interest; and correlating the ratio of spectral measurements to the surface parameters of interest.

2. The method according to claim 1 wherein the surface parameters are selected from the group consisting of vegetation cover, vegetation density, and combinations thereof.

3. The method according to claim 1 wherein the surface parameters are selected from the group consisting of suspended sediment concentration in water, turbidity in water, and combinations thereof.

4. The method according to claim 1 wherein the spectral bands measurements for the two immediate applications are visible red and near-infrared.

5. The method according to claim 1 wherein the ratioing techniques comprising the following formula:

$$Radiance(red) =$$
$$Reflectance(red) \times Eo(red) / Radiance(nir) = Reflectance(nir) \times Eo(nir)$$

wherein Eo is the total solar irradiance in a given spectral band is used in place of spectral reflectances.

6. The method according to claim 1 wherein the spectral measurments are collected at time intervals ranging from about 15 minutes to two weeks during daylight.

7. A method for monitoring surface parameters comprising collecting a plurality of spectral radiance measurements in two spectral bands using a plurality of one to several radiometers covering different portions of the spectrum;

applying ratioing techniques to the spectral radiance measurements to remove the effect of sun elevation and cloud cover variations and obtain a ratio of spectral radiance measurements wherein the ratio of spectral radiance measurements comprise a direct correlation to spectral reflectance values;

monitoring the surface parameters of interest; and correlating the ratio of spectral radiance measurements to the surface parameters of interest.

8. The method according to claim 7 wherein the surface parameters are selected from the group consisting of vegetation cover, vegetation density, and combinations thereof.

9. The method according to claim 7 wherein the surface parameters are selected from the group consisting of suspended sediment concentration in water, turbidity in water, and combinations thereof.

10. The method according to claim 7 wherein the spectral bands measurements for the two immediate applications are visible red and near-infrared.

11. The method according to claim 7 wherein the ratioing techniques comprising the following formula:

$$Radiance(red) =$$
$$Reflectance(red) \times Eo(red) / Radiance(nir) = Reflectance(nir) \times Eo(nir)$$

wherein Eo is the total solar irradiance in a given spectral band is used in place of spectral reflectances.

12. The method according to claim 7 wherein the spectral measurments are collected at time intervals ranging from about 15 minutes to two weeks during daylight.

\* \* \* \* \*